US008645157B2

(12) United States Patent
Giles et al.

(10) Patent No.: US 8,645,157 B2
(45) Date of Patent: Feb. 4, 2014

(54) METHODS AND SYSTEM TO IDENTIFY EXAMS WITH SIGNIFICANT FINDINGS

(75) Inventors: Stephan Giles, Middlebury, VT (US); Kimberly Stavrinakis, Richmond, VT (US); Timothy Fitzgerald, Burlington, VT (US); Juan deCos, Boston, MA (US)

(73) Assignee: General Electric Company, Schenectady, NY (US)

( * ) Notice: Subject to any disclaimer, the term of this patent is extended or adjusted under 35 U.S.C. 154(b) by 524 days.

(21) Appl. No.: 12/395,403

(22) Filed: Feb. 27, 2009

(65) Prior Publication Data

US 2010/0223067 A1 Sep. 2, 2010

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC .......................................................... 705/2, 3
See application file for complete search history.

(56) References Cited

U.S. PATENT DOCUMENTS

| | | | |
|---|---|---|---|
| 6,029,138 A * | 2/2000 | Khorasani et al. ................ 705/2 |
| 6,785,410 B2 | 8/2004 | Vining et al. |
| 6,819,785 B1 | 11/2004 | Vining et al. |
| 7,297,111 B2 | 11/2007 | Iliff |
| 7,308,126 B2 | 12/2007 | Rogers et al. |
| 2004/0078215 A1* | 4/2004 | Dahlin et al. ..................... 705/2 |
| 2004/0151358 A1* | 8/2004 | Yanagita et al. ............. 382/132 |
| 2005/0171940 A1* | 8/2005 | Fogg et al. ........................ 707/3 |
| 2007/0076929 A1* | 4/2007 | Gentles et al. ................ 382/128 |
| 2008/0004505 A1* | 1/2008 | Kapit et al. .................... 600/300 |
| 2008/0028036 A1* | 1/2008 | Slawson et al. ............... 709/217 |
| 2008/0069477 A1* | 3/2008 | Engels et al. ................. 382/291 |
| 2009/0083074 A1* | 3/2009 | Shioe .............................. 705/3 |
| 2009/0274384 A1* | 11/2009 | Jakobovits ................... 382/254 |

* cited by examiner

*Primary Examiner* — Neha Patel
(74) *Attorney, Agent, or Firm* — Hanley, Flight & Zimmerman

(57) ABSTRACT

Methods and system to identify similar exams are described. An example computer-implemented method to identify similar exams includes selecting a category. Additionally, the example method includes comparing the selected category to records associated with exams to identify any of the exams that include information related to the category. Further, the example method includes displaying the exams identified as related to the category to a healthcare practitioner. Further still, the example method includes visually differentiating at least one of the displayed exams based on a significance level associated with the at least one of the displayed exams.

11 Claims, 9 Drawing Sheets

FIG. 5B

Continuous Medications

| Med. name | Dose | Units | Route | Freq. | Start date |
|---|---|---|---|---|---|
| HUMULIN 50 | 1 | LML | INTRA ART | milliliters | 07/28/2006 |

533

Post-procedure Medications
No active post-procedure medication records for the exam on file. ~534

Protocol

| Code | Description |
|---|---|

Comments

Exams ▢ exams ~526

550

| ▽ Significance | ○ Exam | Accession | ○ Sts | ▽ Date/Time |
|---|---|---|---|---|
| ▨ | ABDOMEN | 104243 | P | 11/12/2008 2:05 PM |
| ▯ | ABDOMEN | 104247 | F | 11/12/2008 2:03 PM |
| ▯ | ABDOMEN | 104239 | F | 11/16/2008 10:00 AM |
| ▦ | ABDOMEN | 104249 | F | 11/16/2008 10:00 AM |
| ▨ | ABDOMEN | 104241 | F | 11/16/2008 10:00 AM |

540 542 544 546 548

Current Diagnostic Report Text - All 104246
Signs and Symptoms:
History:
Scheduling Comments:
Pt. Loc:          Phone:
Performign Provider Comments:
▲ Attending: giles, steve
▲ Requester: giles, steve
Clinical History  ~536
This is a test
Comparison

METHODS AND SYSTEM TO IDENTIFY EXAMS WITH SIGNIFICANT FINDINGS

BACKGROUND

Healthcare environments, such as hospitals and clinics, typically include information systems (e.g., hospital information systems (HIS), radiology information systems (RIS), storage systems, picture archiving and communication systems (PACS), electronic medical records (EMR)) to manage clinical information, management information, financial information, and/or scheduling information. The information may be centrally stored or divided into a plurality of locations. Healthcare practitioners may desire to access patient information at various points in a healthcare workflow. For example, during an encounter with a patient, medical personnel may access patient information, such as a patient's medical history and/or a patient's symptoms in an ongoing medical procedure. Alternatively, medical personnel may enter new information, such as history, diagnostic, or treatment information, into a medical information system during an ongoing medical procedure.

Medical practitioners, such as doctors, surgeons, and other medical professionals, rely on clinical information stored in such systems during an encounter(s) with a patient, for example, to assess the condition of a patient, to provide immediate treatment in an emergency situation, to diagnose a patient and/or to provide any other medical treatment or attention. Additionally, in some instances, it is helpful for healthcare practitioners to review other similar exams to assist in clinical decision support. However, known systems are unable to identify similar exams with significant findings and, thus, healthcare practitioners must parse through volumes of material to identify such similar exams. As a result, the efficiency of the healthcare practitioner is compromised.

SUMMARY

In one example implementation, an example computer-implemented method to identify similar exams includes selecting a category. Additionally, the example method includes comparing the selected category to records associated with exams to identify any of the exams that include information related to the category. Further, the example method includes displaying the exams identified as related to the category to a healthcare practitioner. Further still, the example method includes visually differentiating at least one of the displayed exams based on a significance level associated with the at least one of the displayed exams.

In another example implementation, an example medical information system includes a data store in communication with one or more data entry systems to receive and store records associated with exams. Additionally, the example medical information system includes an identifier to compare a selected category associated with a modality and a body site to the records associated with the exams to identify whether any of the exams include information related to the category. Further, the example medical information system includes an indicator to indicate a significance level associated with the identified exams. Further still, the example medical information system includes a display module to convey the identified exams to a user interface.

BRIEF DESCRIPTION OF THE DRAWINGS

FIG. 6 is another screenshot of an example user interface used to convey the medical information stored and communicated in the example medical information system of FIG. 1.

Figure 1:
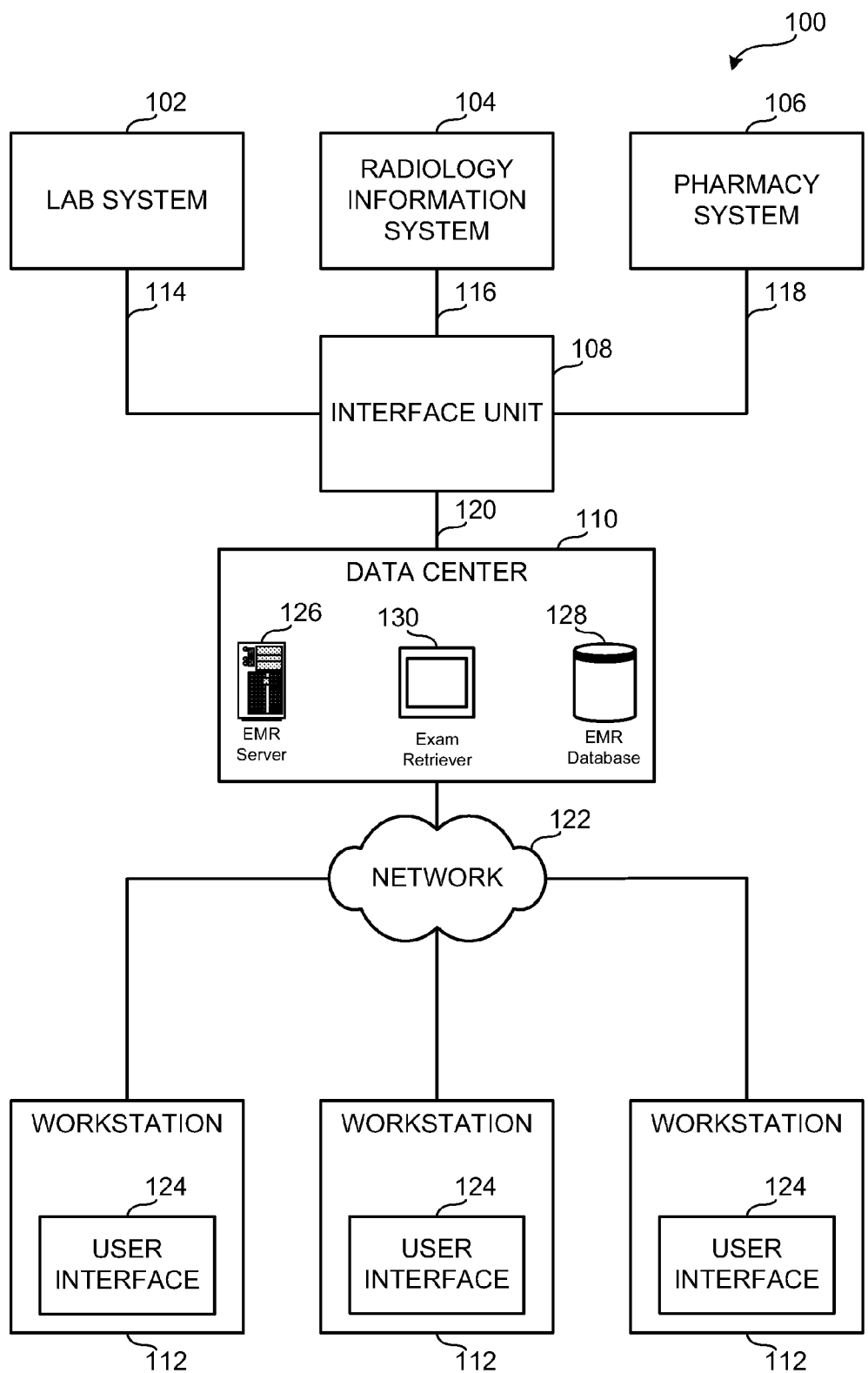
FIG. 1 is a block diagram of an example medical information system.

The foregoing summary, as well as the following detailed description of certain example implementations, will be better understood when read in conjunction with the appended drawings. For the purpose of illustrating the example methods and systems described herein, certain implementations are shown in the drawings. It should be understood, however, that the example methods and systems are not limited to the arrangements and instrumentality shown in the attached drawings.

DETAILED DESCRIPTION

Although the following discloses example methods, apparatus, systems, and articles of manufacture including, among other components, firmware and/or software executed on hardware, it should be noted that such methods, apparatus, systems and articles of manufacture are merely illustrative and should not be considered as limiting. For example, it is contemplated that any or all of these firmware, hardware, and/or software components could be embodied exclusively in hardware, exclusively in software, exclusively in firmware, or in any combination of hardware, software, and/or firmware. Accordingly, while the following describes example methods, apparatus, systems, and/or articles of manufacture, the examples provided are not the only way(s) to implement such methods, apparatus, systems, and/or articles of manufacture.

The examples described herein describe example clinical workflows. In particular, the examples described herein identify significant findings associated with exams by, for example, comparing extracted data from exams with known significant findings. Additionally, the examples described herein determine and associate a significance level to each of the exams based on the particular significance levels assigned to the corresponding known significant findings. Further, the examples described herein automatically add exams associated with a particular significance level to a worklist as well as communicate such exams to associated healthcare practitioners. Additionally, the examples described herein store the exams associated with the particular significance level in a data store. Such an approach supports workflows that enable significant findings to be identified, documented and communicated, which advantageously enables such workflows to be relatively easily audited.

Additionally, the example methods and system described herein identify similar exams based on a selected category to advantageously enable healthcare practitioners to more quickly and efficiently obtain and review the most relevant exams to assist in clinical decision support. In particular, the example methods and system described herein compare a selected category to information contained in records associated with exams to identify if any of the exams include information related to the category. Additionally, the example methods and system described herein convey information related to the exams identified as related to the category to workstations to enable a healthcare practitioner to review the identified exams. Further, the methods and system described herein visually differentiate at least some of the exams by, for example, a color code, based on a significance level associated with the particular exam. Such an approach decreases the likelihood that critical information is missed or mistakenly overlooked during a patient encounter and, thus, the quality of delivered patient care is increased.

FIG. 1 is a block diagram of an example medical information system 100 capable of implementing the example methods and apparatus described herein to assign significance levels to exams, to identify similar exams based on a selected category and/or to support a significant findings workflow. Specifically, the medical information system 100 includes a lab system 102, a radiology information system 104, and a pharmacy system 106. Additionally, the medial information system 100 includes an interface unit 108, a data center 110, and a plurality of workstations 112. In the illustrated example, the lab system 102, the radiology information system 104, and the pharmacy system 106 are housed in a healthcare facility and locally archived. However, in other implementations, the lab system 102, the radiology information system 104, and the pharmacy system 106 may be housed in one or more other suitable locations. Furthermore, one or more components of the medical information system 100 may be combined and/or implemented together. For example, the lab system 102 and/or the radiology information system 104 may be integrated with the pharmacy system 106; the radiology information system 104 may be integrated with the pharmacy system 106; and/or the three example information systems 102, 104 and/or 106 may be integrated together. In other example implementations, the medical information system 100 includes a subset of the illustrated information systems 102, 104 and/or 106. For example, the medical information system 100 may include only one or two of the lab system 102, the radiology information system 104, and the pharmacy system 106. Preferably, information (e.g., test results, observations, diagnosis, etc.) is entered into the lab system 102, the radiology information system 104, and the pharmacy system 106 by healthcare practitioners (e.g., radiologists, physicians, and/or technicians) before, during and/or after a patient examination and/or encounter.

The lab system 102 receives, stores and/or conveys medical information received from, for example, personnel at a hospital, clinic, and/or a physician's office associated with the Clinical Laboratory Department, which includes information related to Anatomic Pathology, Clinical Microbiology, Clinical Biochemistry, Hematology, etc. The radiology information system 104 stores information such as, for example, radiology reports, messages, warnings, alerts, patient scheduling information, patient demographic data, patient tracking information, and/or physician and patient status monitors. Additionally, the radiology information system 104 enables exam order entry (e.g., ordering an x-ray of a patient) and image and film tracking (e.g., tracking identities of one or more people that have checked out a film). In some examples, information in the radiology information system 104 is formatted according to the HL7 (Health Level Seven) clinical communication protocol.

The pharmacy system 106 receives, stores and/or conveys medical information associated with orders for medications. In some examples, the pharmacy system 106 tracks medication orders to completion, generates medical bills associated with the medication dispensed, and monitors and/or controls the inventory in the pharmacy. The pharmacy system 106 interfaces with a number of other systems within the medical information system 100 to receive prescription orders and to generate medical bills associated with the dispensed medication such as, for example, the data center 110 and an insurance system (not shown).

The interface unit 108 includes a lab system interface connection 114, a radiology information system interface connection 116, a pharmacy system interface connection 118, and a data center interface connection 120. The interface unit 108 facilitates communication among the lab system 102, the radiology information system 104, the pharmacy system 106, and/or the data center 110. The interface connections 114, 116, 118, and 120 may be implemented by, for example, a Wide Area Network (WAN) such as a private network or the Internet. Accordingly, the interface unit 108 includes one or more communication components such as, for example, an Ethernet device, an asynchronous transfer mode (ATM) device, an 802.11 device, a DSL modem, a cable modem, a cellular modem, etc. In turn, the data center 110 communicates with the plurality of workstations 112 via a network 122, implemented at a plurality of locations (e.g., a hospital, clinic, doctor's office, other medical office, or terminal, etc.). The network 122 is implemented by, for example, the Internet, an intranet, a private network, a wired or wireless Local Area Network, and/or a wired or wireless Wide Area Network. In some examples, the interface unit 108 also includes a broker (e.g., a Mitra Imaging's PACS Broker) to allow medical information and medical images to be transmitted together and stored together.

In operation, the interface unit 108 receives images, medical reports, administrative information, and/or other clinical information from the information systems 102, 104, 106 via the interface connections 114, 116, 118. If necessary (e.g., when different formats of the received information are incompatible), the interface unit 108 translates or reformats (e.g., into Structured Query Language (SQL) or standard text) the medical information, such as medical reports, to be properly stored at the data center 110. Preferably, the reformatted medical information may be transmitted using a transmission protocol to enable different medical information to share common identification elements, such as a patient name or a social security number. Next, the interface unit 108 transmits the medical information to the data center 110 via the data center interface connection 120. Finally, medical information is stored in the data center 110.

The medical information is later viewable and easily retrievable at one or more of the workstations 112 (e.g., by their common identification element, such as a patient name or a record number). The workstations 112 may be any equipment (e.g., a personal computer) capable of executing software that permits electronic data (e.g., medical reports) and/or electronic medical images (e.g., x-rays, ultrasounds, MRI scans, etc.) to be acquired, stored, or transmitted for viewing and operation. The workstations 112 may receive commands and/or other inputs from a user via, for example, a microphone, a keyboard, a mouse, a track ball, etc. As described in greater detail below, the workstations 112 are capable of implementing a user interface 124 to enable a healthcare practitioner to interact with the medical information system 100. For example, in response to a category selected by the healthcare practitioner, the user interface 124 may display exams identified as related to the category. The identified exams may be exams associated with the same patient and/or other patients. In other examples, in response to an input by the healthcare practitioner, the user interface 124 may display previous exams for a patient. In still other examples, the workstations 112 may receive a voice input(s) that relates to an encounter between the healthcare practitioner and a patient. In such examples, the workstations 112 may include one or more options related to generating a text string(s) used to generate a medical report(s). Further, in other examples, the user interface 124 may display a worklist of significant findings.

The example data center 110 of FIG. 1 is an archive to store information such as, for example, images, data, medical reports, and/or, more generally, patient medical records. In addition, the data center 110 may also serve as a central conduit to information located at other sources such as, for example, local archives, the lab systems, radiology information systems, and/or pharmacy systems (e.g., the lab system 102, the radiology information system 104, and the pharmacy system 106). That is, the data center 110 may store links or indicators (e.g., identification numbers, patient names, or record numbers) to information. In the illustrated example, the data center 110 is managed by an application server provider (ASP) and is located in a centralized location that may be accessed by a plurality of systems and facilities (e.g., hospitals, clinics, doctor's offices, other medical offices, and/or terminals). In some examples, the data center 110 may be spatially distant from the lab system 102, the radiology information system 104, and the pharmacy system 106 (e.g., at a General Electric® facility).

The example data center 110 of FIG. 1 includes an EMR server 126, an EMR database 128 and an exam retriever 130. The EMR server 126 receives, processes, and conveys information to and from the components of the medical information system 100. The EMR database 128 stores the medical information described herein and provides access thereto. The exam retriever 130 identifies exams that include information related to a selected category and/or identifies previous exams associated with a patient. Specifically, based on a selected category associated with a modality and a body site, the exam retriever 130 compares the selected category to information contained in records associated with exams stored in, for example, the EMR database 128. Such records may be associated with the same and/or different patients. Additionally, the exam retriever 130 identifies if any of the records include information related to the selected category. Further, the exam retriever 130 conveys information related to the exams identified as related to the category to one of the respective workstation 112 to enable a healthcare practitioner to review the identified exams. Further yet, the exam retriever 130 may visually differentiate the exams by, for example, a color code, based on a significance level associated with the particular exam. Such an approach enables healthcare practitioners to efficiently obtain the most relevant information to assist in clinical decision support.

In some examples, the exam retriever 130 generates a medical report in association with an exam based on, for example, a user input(s) and/or a voice input(s). Additionally, the exam retriever 130 identifies and extracts keywords or phrases from the medical report and includes these identified keywords or phrases with a record generated in association with the exam. Further, the exam retriever 130 assigns a significance level to the exam based on the identified keywords or phrases and enables a healthcare practitioner to review and edit the assigned significance level. Further yet, if the significance level is at or above a particular level (e.g., "life threatening," "act upon as soon as possible," etc.), the particular exam is added to a work list and is communicated to other associated healthcare practitioners. Generally, such exams are utilized to populate a significant findings worklist. Further still, the exam retriever 130 identifies if the associated healthcare practitioner has reviewed the communicated exam. Such an approach enables healthcare practitioners to more quickly and efficiently generate and/or record information related to a patient encounter to the respective medical report. Additionally, this approach decreases the likelihood that significant information is mistakenly overlooked and ensures that associated healthcare practitioners are timely notified of exams, which are assigned a particular significance level.

Figure 2:
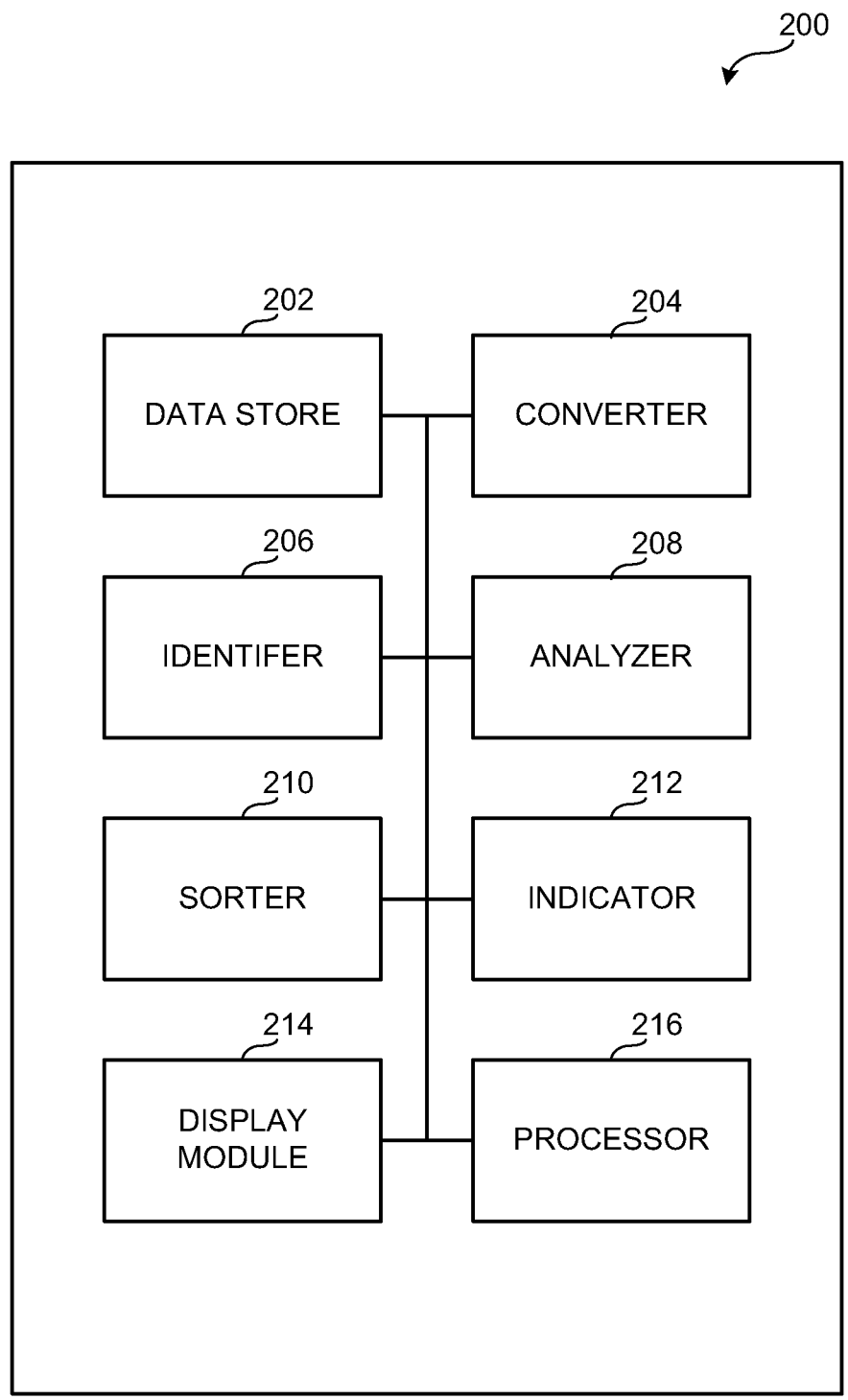
FIG. 2 is a block diagram of an example apparatus that may be used to implement the example exam retriever of FIG. 1.

FIG. 2 is a block diagram of an example exam retriever 200 that may be used to implement the exam retriever 130 of FIG. 1. In the illustrated example of FIG. 2, the example exam retriever 200 includes a data store 202, a converter 204, an identifier 206, an analyzer 208, a sorter 210, an indicator 212, a display module 214 and a processor 216. While an example manner of implementing the exam retriever 130 of FIG. 1 has been illustrated in FIG. 2, one or more of the elements, processes and/or devices illustrated in FIG. 2 may be combined, divided, re-arranged, omitted, eliminated and/or implemented in other ways. Specifically, in some examples, the processor 216 may be integrated into each of the data store 202, the converter 204, the identifier 206, the analyzer 208, the sorter 210, the indicator 212 and/or the display module 214. Further, the data store 202, the converter 204, the identifier 206, the analyzer 208, the sorter 210, the indicator 212, the display module 214, the processor 216 and/or, more generally, the example exam retriever 200 of FIG. 2 may be implemented by hardware, software, firmware and/or a combination of hardware, software and/or firmware. Thus, for example, any of the data store 202, the converter 204, the identifier 206, the analyzer 208, the sorter 210, the indicator 212, the display module 214, the processor 216 and/or, more generally, the example exam retriever 200 of FIG. 2 can be implemented by one or more circuit(s), programmable processor(s), application specific integrated circuit(s) (ASIC(s)), programmable logic device(s) (PLD(s)) and/or field programmable logic device(s) (FPLD(s)), etc. When any of the appended claims are read to cover a purely software and/or firmware implementation, at least one of the data store 202, the converter 204, the identifier 206, the analyzer 208, the sorter 210, the indicator 212, the display module 214, the processor 216 and/or, more generally, the example exam retriever 200 of FIG. 2 are hereby expressly defined to include a tangible medium such as a memory, DVD, CD, etc., storing the software and/or firmware. Further still, the example exam retriever 200 of FIG. 2 may include one or more elements, processes and/or devices in addition to, or instead of, those illustrated in FIG. 2, and/or may include more than one of any or all of the illustrated elements, processes and devices.

To assign a significance level to an exam, initially, the exam retriever 200 conveys a medical report generated in association with an exam and/or a voice input(s) from which a medical report is to be generated to the data store 202. The data store 202 creates a software object to represent the received information. The software object includes a plurality of properties that can be altered by, for example, the data store 202, the converter 204, the identifier 206, the analyzer 208, the sorter 210, the indicator 212, the display module 214 and/or the processor 216. The data store 202 stores the information associated with the medical report(s) and/or the voice input(s) and other related information and receives and stores the identified significant findings and associated significance levels as discussed below.

In some examples, the medical report may be generated by typed commands and/or inputs received by one of the workstations 112 (FIG. 1). However, in other examples, the medical report may be generated from voice inputs received by one of the workstations 112 (FIG. 1) on which a speech-to-text conversion is performed. In such examples, to produce a text string used to generate a medical report, initially, the processor 216 retrieves the voice input(s) from the data store 202 and conveys it to the converter 204. Specifically, the converter 204 performs a speech-to-text conversion on the voice input(s) to generate a text string that represents the voice input(s). The converter 204 may also create a software object to represent the text string. In some examples, the converter 204 compares a portion or portions of the voice input with known voice inputs that are associated with a known word, phrase and/or phrases. As the portion or portions of the voice input are identified as being substantially similar to the known word, phrase and/or phrases, the converter 204 generates a text string that represents the voice input. The generated text string is then utilized by the converter 204 to generate an associated medical report. Once the converter 204 has performed the speech-to-text conversion on the voice input(s) and generated an associated medical report, the medical report and the associated values are retrieved by the processor 216 and conveyed to the data store 202 for storage.

To identify and extract keywords and/or phrases from patient information contained in medical reports (e.g., a plain text record), the processor 216 retrieves the patient information from the data store 202 and conveys it to the identifier 206. In addition, keywords and/or phrases may be identified and/or extracted from electronic medical records (EMRs), optical character recognition (OCR), a medication order system, a database, a computerized physician order entry (CPOE), and/or any other suitable source. The identifier 206 may also create a software object to represent the extracted keywords and/or phrases from the respective medical report. In operation, the identifier 206 implements one or more algorithms capable of scanning the patient information contained in the medical report and identifying one or more keywords, phrases, etc. that are representative of one or more significant findings associated with, for example, a problem, a symptom, a procedure, a diagnosis, or any other relevant treatment information. If the identifier 206 has identified keywords and/or phrases within the patient information, the identifier 206 extracts and associates the data with a medical record for the particular patient. Specifically, the identifier 206 assigns a value to the extracted data and/or the patient information that is associated with the respective medical record. Once the identifier 206 has identified the keywords, and/or phrases within the patient information associated with significant findings, the extracted data and the associated values are retrieved by the processor 216 and conveyed to the data store 202 for storage.

To assign a significance level to exams based on the corresponding identified significant findings, the processor 216 retrieves the keywords and/or phrases from the data store 202 and conveys them to the analyzer 208. The analyzer 208 compares the extracted data to known significant findings assigned particular significance levels, which may be stored in the data store 202. As the analyzer 208 identifies the extracted data as being substantially similar to the known significant findings, the analyzer 208 associates the respective significance level with the associated exam. Specifically, the analyzer 208 assigns a value that is associated with the respective significance level to the exam to which the extracted data is associated. In some examples, the significance level may be, for example, "life threatening," "act upon as soon as possible," "incidental finding to monitor" and/or "no action required." However, the significance level may be any other suitable significance level. Once the analyzer 208 has assigned a significance level to the exam based on the significant findings, the exam and the associated significance level are retrieved by the processor 216 and conveyed to the data store 202 for storage.

The exam retriever 200 then conveys the exam and the associated significance level, along with the associated values via, for example, the display module 214, to the EMR database 128 for storage, where it can later be retrieved using one of the workstations 112 (FIG. 1). Thus, a healthcare practitioner is able to review the significance level to edit and/or verify the accuracy of this information, to save or upload this information to the patient medical report, record or history as, for example, discrete data.

Once the healthcare practitioner has edited and/or verified the accuracy of the information, depending on the significance level associated with the exam, the processor 216 adds the exam to a work list, which includes, for example, outstanding tasks, reports (e.g., diagnostic reports) containing significant findings and/or reports containing particular significance levels. Additionally, the processor 216 automatically communicates the exam to associated healthcare practitioners (e.g., a referring physician, other involved physicians, etc.). In some examples, a time period between when a significant finding is identified and when the significant finding is communicated to the associated healthcare practitioners may vary depending on the significance level associated with the exam. For example, if the significance level is "life threatening," the significant findings associated with the exam will be communicated immediately to the associated healthcare practitioners. However, if the significance level is an "incidental finding to monitor," there may be a longer period of time between when the significant findings are identified and when they are communicated to the associated healthcare practitioners. Further, as the associated healthcare practitioners access and/or view the communicated exam(s), the identifier 206 identifies that the exam has been reviewed by the respective healthcare practitioner, which enables the exam retriever 200 to filter and/or audit a list of communicated exams to identify which of the communications has been completed (i.e., the healthcare practitioner has reviewed the exam).

To identify previous exams associated with a patient, initially, a user inputs a patient ID and/or name into one of the workstations 112 (FIG. 1). The exam retriever 200 receives and then conveys this information to the data store 202. The processor 216 retrieves this information from the data store 202 and conveys it to the identifier 206. The identifier 206 identifies previous exams associated with the patient by, for example, comparing the patient ID and/or name with patient IDs and/or names associated with exams stored in, for example, the data store 202. If the identifier 206 identifies an exam(s) that is associated with the particular patient, the identifier 206 populates a list (e.g., a data structure capable of storing a plurality of exam identifiers) with the identified previous exam(s). Once the previous exams associated with the patient are identified, the identified exams and associated values are retrieved by the processor 216 and conveyed to the data store 202 for storage.

To sort the identified previous exams, the processor 216 retrieves this information from the data store 202 and conveys it to the sorter 210. The sorter 210 sorts the different exams based on, for example, a time at which the exam occurred and/or a significance level associated with the exam. Once the sorter 210 has sorted the identified previous exams, the sorted exams are retrieved by the processor 216 and conveyed to the data store 202 for storage.

To indicate a significance level associated with the identified previous exams, the processor 216 retrieves the sorted exams and conveys them to the indicator 212. The indicator 212 may indicate an associated significance level by, for example, associating a particular color and/or font with each significance level. Specifically, the indicator 212 assigns a value to each significance level, which corresponds to a degree of severity or importance. For example, the color red may indicate "life threatening," the color orange may indicate to "act upon as soon as possible," the color yellow may indicate "incidental findings to monitor" and the color green may indicate "no action required." Once the indicator 212 has indicated the significance level associated with the identified previous exams, the identified previous exams and the associated values are retrieved by the processor 216 and conveyed to the data store 202 for storage.

The exam retriever 200 then conveys the identified exams, along with the associated values via, for example, the display module 214, to the EMR database 128 for storage, where it can later be retrieved using one of the workstations 112 (FIG. 1). Thus, a healthcare practitioner is able to access one or more exams to view previous clinical information, results and/or images related to the patient. In some examples, the identified exams are displayed in a longitudinal record to enable the healthcare practitioner to more easily review the displayed information and/or to obtain the most relevant information desired by the healthcare practitioner. Enabling the healthcare practitioner to review previous exams for a patient, helps the healthcare practitioner to better evaluate a current exam and to accurately identify significant findings (e.g., a level of findings) contained in a report generated in association with the current exam. As discussed above, depending on the significant findings contained within the report, different significance levels, which may correspond to different colors, are assigned to the exam. Once the current exam is assigned a significance level by, for example, the healthcare practitioner and/or via the examples described herein, the identifier 206 may identify which of the identified previous exams are the most relevant (e.g., add value) to the current exam being interpreted and/or reviewed by the healthcare practitioner.

To identify similar exams based on a selected category, initially, a user selects and/or inputs a category into one of the workstations 112 (FIG. 1). Specifically, a user may select a category associated with a modality and a body region, site or part (e.g., chest). While the examples described herein discuss selecting a category associated with a modality and a body site, the category may additionally or alternatively be associated with the responsible provider, the patient name, the medical record, significance level, subspecialty, etc., for example. The exam retriever 200 receives the information related to the category and conveys it to the data store 202. The data store 202 creates a software object to represent the received information. The software object includes a plurality of properties that can be altered by, for example, the data store 202, the converter 204, the identifier 206, the analyzer 208, the sorter 210, the indicator 212, the display module 214 and/or the processor 216. The data store 202 stores the information associated with the selected category and other related information and receives and stores the identified exams that include information related to the category as discussed below.

To compare the selected category to records associated with exams to identify whether any of the exams include information related to the selected category, the processor 216 retrieves the information associated with the selected category from the data store 202 and conveys it to the identifier 206. Specifically, the identifier 206 compares a modality and body region, site or part associated with the selected category to other exams, which may be stored in the data store 202. The other exams may be exams associated with a particular patient or other patients. If the identifier 206 identifies an exam(s) that includes information related to the selected category, the identifier 206 populates a list (e.g., a data structure capable of storing a plurality of exam identifiers) with the identified exam(s). In some examples, the healthcare practitioner may direct the identifier 206 to identify exams having a particular significance level(s). Additionally and/or alternatively, the healthcare practitioner may direct the identifier 206 to identify exams that occurred within a particular time frame such as, for example, between Oct. 25, 2008 and Nov. 25, 2008. Identifying exams that include information related to the selected category enables healthcare practitioners to readily identify and review the most pertinent information to assist in decision support, which increases the overall efficiency of the healthcare practitioner and reduces the likelihood that significant information is mistakenly overlooked. Once the identifier 206 has identified the exams that include information related to the selected category, the identified exams and associated values are retrieved by the processor 216 and conveyed to the data store 202 for storage.

To sort the identified exams based on a corresponding significance level, for example, the processor 216 retrieves the identified exams and the associated values and conveys them to the sorter 210. The sorter 210 sorts the different exams based on the corresponding significance level. As discussed above, the significance level may be "life threatening," "act upon as soon as possible," "incidental finding to monitor" and/or "no action required," for example. In some instances, the sorter 210 may sort the identified exams to reflect the urgency of the significance level such as, for example, exams associated with a significance level of "life threatening" may be positioned toward a top of a list while exams associated with a significance level of "no action required" may be positioned toward the bottom of the list. In other examples, the sorter 210 may sort the identified exams to reflect the relevancy of the exam. In such examples, exams identified as being the most relevant may be positioned toward the top of the list and exams identified as not being as relevant may be positioned toward the bottom of the list. The sorted exams can be advantageously used in clinical decision support by enabling a healthcare practitioner to readily identify the exams that are the most relevant to the selected category and/or contain relatively urgent significance levels. Once the sorter 210 has sorted the identified exams, the sorted exams are retrieved by the processor 216 and conveyed to the data store 202 for storage.

To indicate a significance level associated with the identified exams, the processor 216 retrieves the sorted exams and conveys them to the indicator 212. The indicator 212 may indicate the associated significance level by, for example, associating a particular color and/or font with each significance level. Specifically, the indicator 212 assigns a value to each significance level, which corresponds to a degree of severity or importance. For example, the color red may indicate "life threatening," the color orange may indicate to "act upon as soon as possible," the color yellow may indicate "incidental findings to monitor" and the color green may indicate "no action required." Once the indicator 212 has indicated the significance level associated with the identified exams, the identified exams and the associated values are retrieved by the processor 216 and conveyed to the data store 202 for storage.

The exam retriever 200 then conveys the identified exams, along with the associated values via, for example, the display module 214, to the EMR database 128 for storage. In some examples, the display module 214 may contain a filter (e.g., a redaction module) that identifies information contained in the identified exams that may raise privacy and/or confidentiality concerns. If the display module 214 identifies information contained in the identified exams that may raise privacy and/or confidentiality concerns, the display module 214 may redact and/or omit this information prior to conveying the identified exams to the EMR database 128. Such an approach ensures compliance with the Health Insurance Portability and Accountability Act (HIPAA) and/or any other regulatory statue(s). The identified exams, along with the associated values may be retrieved using one of the workstations 112 (FIG. 1) and, thus, a healthcare practitioner is able to access one or more exams to view previous clinical information, results and/or images. In some examples, the identified exams are displayed in a longitudinal record to enable the healthcare practitioner to more easily review the displayed information and/or to obtain the most relevant information desired by the healthcare practitioner.

Figure 3:
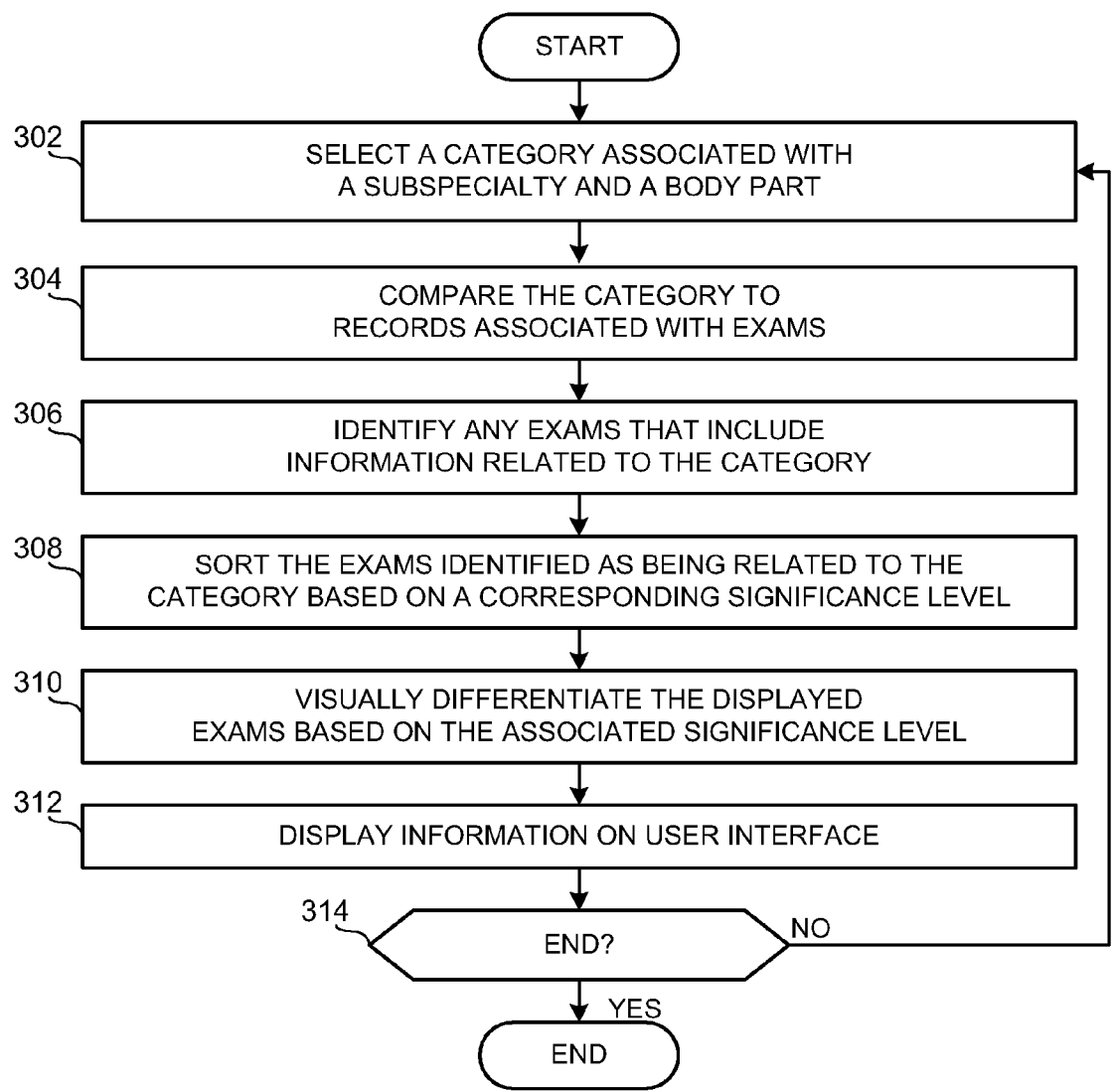
FIG. 3 is a flow diagram representative of example machine readable instructions that may be executed to implement the example exam retriever of FIGS. 1 and/or 2.
Figure 4:
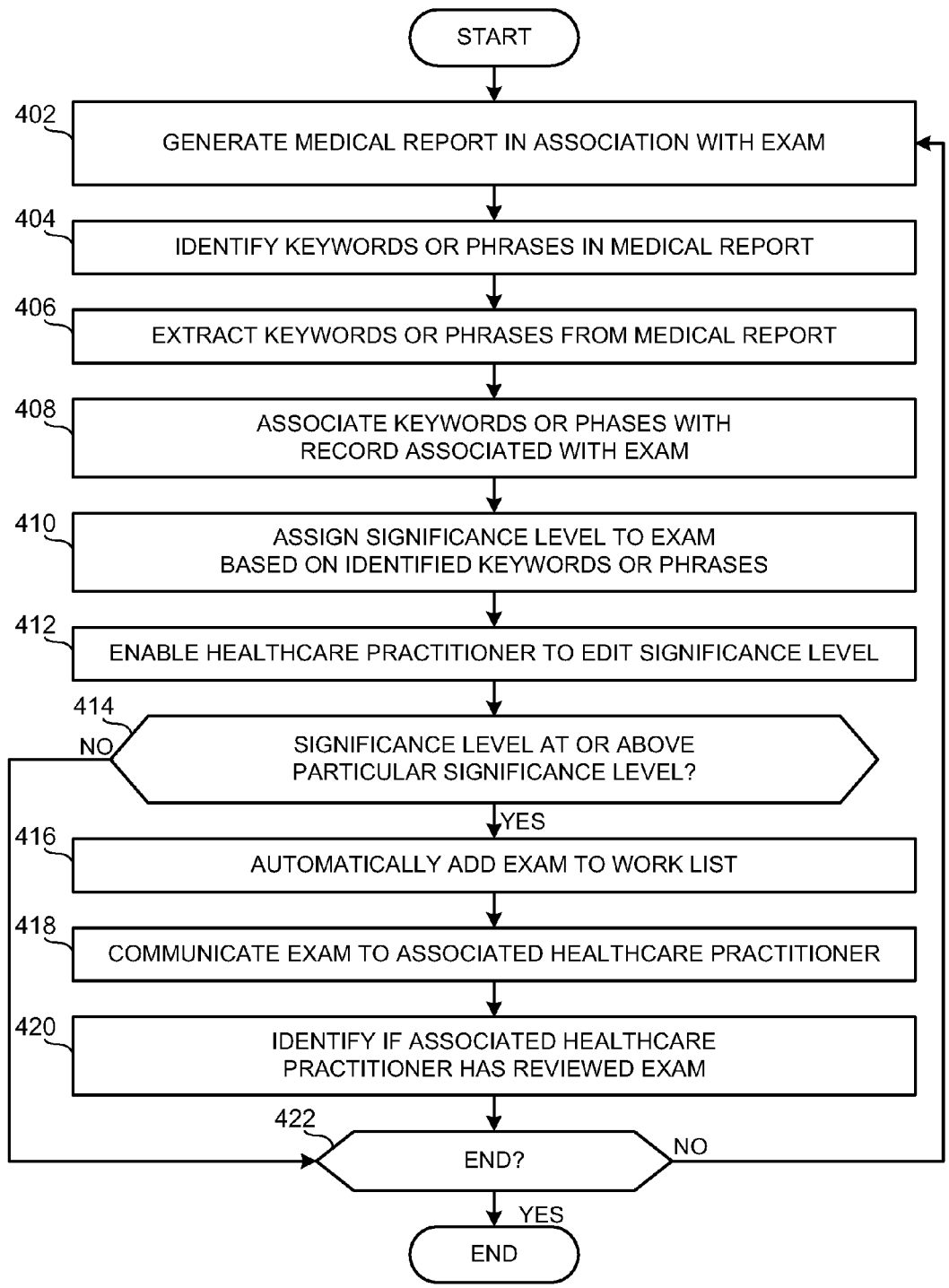
FIG. 4 is another flow diagram representative of example machine readable instructions that may be executed to implement the example exam retriever of FIGS. 1 and/or 2.

The flow diagrams depicted in FIGS. 3 and 4 are representative of machine readable instructions that can be executed to implement the example methods and apparatus described herein. In particular, FIGS. 3 and 4 depict flow diagrams representative of machine readable instructions that may be executed to implement the example exam retriever 130 or 200 of FIGS. 1 and/or 2 to assign significance levels to exams and/or to identify similar exams based on a selected category. The example processes of FIGS. 3 and 4 may be performed using a processor, a controller and/or any other suitable processing device. For example, the example processes of FIGS. 3 and 4 may be implemented in coded instructions stored on a tangible medium such as a flash memory, a read-only memory (ROM) and/or random-access memory (RAM) associated with a processor (e.g., an example processor system 800 discussed below in connection with FIG. 8). Alternatively, some or all of the example processes of FIGS. 3 and 4 may be implemented using combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIGS. 3 and 4 may be implemented manually or as combination(s) of any of the foregoing techniques, for example, any combination of firmware, software, discrete logic and/or hardware. Further, although the example processes of FIGS. 3 and 4 are described with reference to the flow diagrams of FIGS. 3 and 4, other methods of implementing the processes of FIGS. 3 and 4 may be employed. For example, the order of execution of the blocks may be changed, and/or some of the blocks described may be changed, eliminated, sub-divided, or combined. Additionally, any or all of the example processes of FIGS. 3 and 4 may be performed sequentially and/or in parallel by, for example, separate processing threads, processors, devices, discrete logic, circuits, etc.

Turning to FIG. 3, initially, a user selects and/or inputs a category into one of the workstations 112 (FIG. 1) (block 302). Specifically, a user may select a category associated with a modality (e.g., computed tomography (CT)) and a body region, site or part (e.g., chest, spine). The exam retriever 130 and/or 200 (FIGS. 1 and 2) receives this information and the identifier 206 then compares the selected category to records associated with exams (block 304) to identify any exams that include information related to the category (block 306). If the identifier 206 identifies an exam(s) that includes information related to the selected category, the identifier 206 populates a list (e.g., a data structure capable of storing a plurality of exam identifiers) with the identified exam(s). The sorter 210 then sorts the identified exams based on the corresponding significance level (block 308). As discussed above, the significance level may be "life threatening," "act upon as soon as possible," "incidental finding to monitor" and/or "no action required," for example.

In some examples, after the identified exams are sorted, the indicator 206 may indicate the associated significance level by visually differentiating the displayed exams based on the associated significance level (block 310). Specifically, the indicator 212 assigns a value to each significance level, which corresponds to a degree of severity or importance. For example, the color red may indicate "life threatening," the color orange may indicate to "act upon as soon as possible," the color yellow may indicate "incidental findings to monitor" and the color green may indicate "no action required," for example.

The exam retriever 200 then conveys the identified exams, along with the associated values via, for example, the display module 214, to the EMR database 128 for storage. As discussed above, the display module 214 may contain a filter (e.g., a redaction module) that identifies information contained in the identified exams that may raise privacy and/or confidentiality concerns. If the display module 214 identifies information contained in the identified exams that may raise privacy and/or confidentiality concerns, the display module 214 may redact and/or omit this information prior to conveying the identified exams to the EMR database 128. The identified exams, along with the associated values may be retrieved using one of the workstations 112 (FIG. 1) and then displayed on the corresponding user interface 124 (block 312). Thus, a healthcare practitioner is able to access one or more exams to view previous clinical information, results and/or images.

The example processes of FIG. 3 then determines whether another category has been selected (block 314). Otherwise, the example processes of FIG. 3 are ended.

Turning to FIG. 4, initially a medical report is generated in association with an exam (block 402). In some examples, the medical report may be generated by typed commands and/or inputs received by one of the workstations 112 (FIG. 1). However, in other examples, the medical report may be generated from voice inputs received by one of the workstations 112 (FIG. 1) on which a speech-to-text conversion is performed. In such examples, the converter 204 performs a speech-to-text conversion on the voice input(s) to generate a text string that represents the voice input(s). After the text string is generated, the generated text string is utilized by the converter 204 to generate an associated medical report.

After the medical report is generated, the identifier 206 implements one or more algorithms capable of scanning the patient information contained in the medical report to identify one or more keywords, phrases, etc. (block 404) that are representative of one or more significant findings. If the identifier 206 has identified keywords and/or phrases within the patient information, the identifier 206 extracts the identified keywords or phrases from the medical report (block 406) and then associates the identified keywords or phrases with a medical record generated in association with an exam (block 408).

The analyzer 208 then compares the extracted data to known significant findings assigned particular significance levels. As the analyzer 208 identifies the extracted data as being substantially similar to the known significant findings, the analyzer 208 assigns a significance level to the exam based on the identified keywords or phrases (block 410). As described above, the significance level may be, for example, "life threatening," "act upon as soon as possible," "incidental finding to monitor" and/or "no action required."

Once the analyzer 208 assigns a significance level to the exam, the exam retriever 200 conveys the exam and the associated significance level, along with the associated values via, for example, the display module 214, to the EMR database 128 for storage, where it can later be retrieved using one of the workstations 112 (FIG. 1). Thus, a healthcare practitioner is able to review the significance level to edit and/or verify the accuracy of the significance level (block 412).

The processor 216 then determines if the significance level is at or above a predetermined level (block 414). In some examples, the particular significance level may be, for example, "incidental finding to monitor." However, in other examples, the particular significance level may be, for example, "act upon as soon as possible." If the significance level is below the predetermined level, control moves to block 422. However, if the significance level is at or above the particular significance level, the processor 216 automatically adds the exam to a work list (block 416), which includes, for example, outstanding tasks, reports (e.g., diagnostic reports) containing significant findings and/or reports containing particular significance levels. Additionally, the processor 216 communicates the exam to associated healthcare practitioners (e.g., a referring physician, other involved physicians, etc.) (block 418). Further, as the associated healthcare practitioners access and/or view the communicated exam(s), the identifier 206 identifies if the exam has been reviewed by the respective healthcare practitioner (block 420), which enables the exam retriever 200 to filter and/or audit a list of communicated exams to identify which of the communications has been completed (i.e., the healthcare practitioner has reviewed the exam).

The example processes of FIG. 4 then determines whether another medical report is to be generated in association with an exam (block 422). Otherwise, the example processes of FIG. 4 are ended.

Figure 5A:
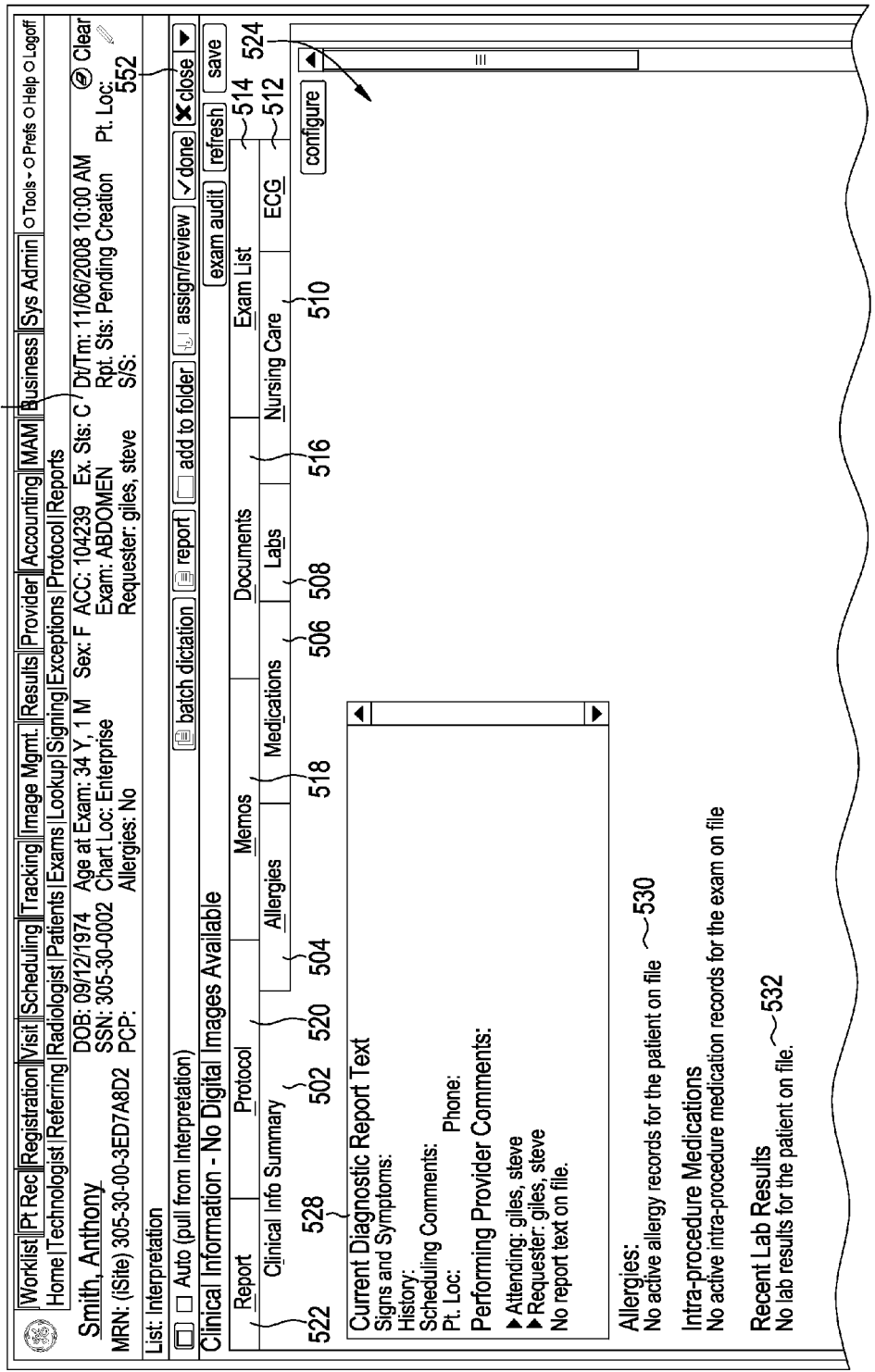
FIG. 5, consisting of FIGS. 5A and 5B, is a screenshot of an example user interface used to convey the medical information stored and communicated in the example medical information system of FIG. 1.

FIG. 5 depicts an example user interface 500 that includes, among other things, tool bars 502, 504, 506, 508, 510, 512, 514, 516, 518, 520, and 522 which provide access to configuration menus, navigation tools, viewing tools, imaging applications, file management tools, etc. The tool bars 502, 504, 506, 508, 510, 512, 514, 516, 518, 520, and 522 may include additional icons and/or functionalities or less icons and/or functionalities than are shown in connection with the user interface 500.

The user interface 500 includes a display area 524 for displaying information related to a patient medical report and/or record and a list of identified previous exams 526. Specifically, in this example, the display area 524 includes a plurality of data fields that correspond to current diagnostic report text 528, allergies 530, recent lab results 532, continuous medications 533, post-procedure medications 534, the list of identified previous exams 526 and clinical history 536. However, other example user interfaces may be implemented having any other number of data fields (e.g., 1, 2, 3, 4, 5, etc.) that correspond to any other topic. Additionally, the display area 524 includes a header 538 that may be associated with general patient information (e.g., date of birth, age at exam, social security number, etc.).

In practice, after a healthcare practitioner enters a patient ID or name into one of the workstations, the patient's electronic medical record is opened and the healthcare practitioner may select the tool bar 502 associated with clinical info summary to review data fields associated with the patient. In particular, the healthcare practitioner may review the list of identified previous exams 526, which, in this example, includes a first exam 540, a second exam 542, a third exam 544, a fourth exam 546 and a fifth exam 548. Each of the exams 540-548 is associated with a corresponding significance level and a particular color code, which is visually depicted in a significance data field 550. For example, the first exam 540 may have been assigned a significance level of "life threatening" and be associated with a first color (e.g., red), the second and third exams 542 and 544 may have been assigned a significance level of "act upon as soon as possible" and be associated with a second color (e.g., orange), the fourth exam 546 may have been assigned a significance level of "incidental finding to monitor" and be associated with a third color (e.g., yellow) and the fifth exam 548 may have been assigned a significance level of "no action required" and be associated with a fourth color (e.g., green). Additionally and/or alternatively, the healthcare practitioner may select any of the other tool bars 504, 506, 508, 510, 512, 514, 516, 518, 520 or 522 to review more detailed information relating to the particular patient. After the healthcare practitioner has reviewed and/or verified the information, the healthcare practitioner may select a close icon 552 to exit from the particular patient's electronic medical record.

Figure 6:
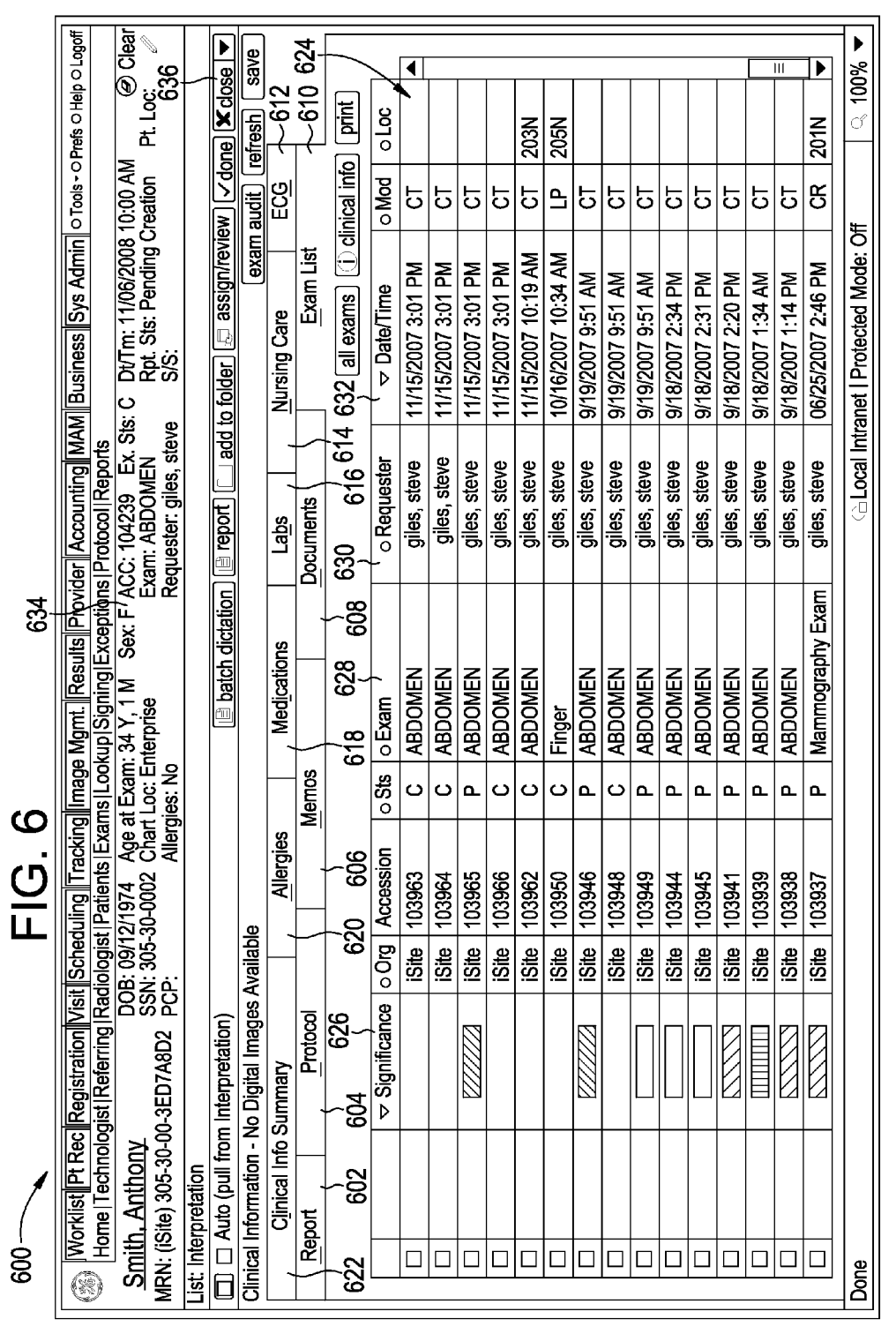

FIG. 6 depicts an example user interface 600 that includes, among other things, tool bars 602, 604, 606, 608, 610, 612, 614, 616, 618, 620, and 622 which provide access to configuration menus, navigation tools, viewing tools, imaging applications, file management tools, etc. The tool bars 602, 604, 606, 608, 610, 612, 614, 616, 618, 620, and 622 may include additional icons and/or functionalities or less icons and/or functionalities than are shown in connection with the user interface 600. Additionally, the tool bars 602, 604, 606, 608, 610, 612, 614, 616, 618, 620, and 622 may be the same and/or substantially similar to the tool bars 502, 504, 506, 508, 5 10, 512, 514, 516, 518, 520, and 522 of FIG. 5. However, as depicted in FIG. 6, the tool bar 610 associated with exam list is selected instead of the tool bar 622 associated with clinical info summary.

The user interface 600 includes a display area 624 for displaying information related to the identified previous exams. Specifically, in this example, the display area 624 includes a plurality of data fields or categories in which corresponding information from the corresponding exam may be positioned adjacent to. Some of the data fields and/or categories may correspond to a significance icon 626, an exam icon 628, a requester icon 630 and a date/time icon 632. However, other example user interfaces may be implemented having any other number of data fields (e.g., 1, 2, 3, 4, 5, etc.) that correspond to any other topic. Additionally, the display area 624 includes a header 634 that may be associated with general patient information (e.g., date of birth, age at exam, social security number, etc.).

In practice, after a healthcare practitioner enters a patient ID or name into one of the workstations 112, the patient's electronic medical record is opened and the healthcare practitioner may select the tool bar 610 associated with exam list to review data fields associated with the patient. In particular, the healthcare practitioner may review the list of identified previous exams. At least some of the identified exams may be assigned a corresponding significance level assigned a particular color code (e.g., red, orange, yellow, green, etc.). The healthcare care practitioner may sort the list of identified previous exams by, for example, selecting one of the data fields 626, 628, 630 and/or 632, for example. For example, if the healthcare practitioner selects the significance icon 626, the identified exams may be sorted based on the associated significance level. Alternatively, if the healthcare practitioner selects the date/time icon 632, the identified exams may be sorted based on the time at which the exam occurred. After the healthcare practitioner has reviewed and/or verified the information, the healthcare practitioner may select a close icon 636 to exit from the particular patient's electronic medical record.

Figure 7:
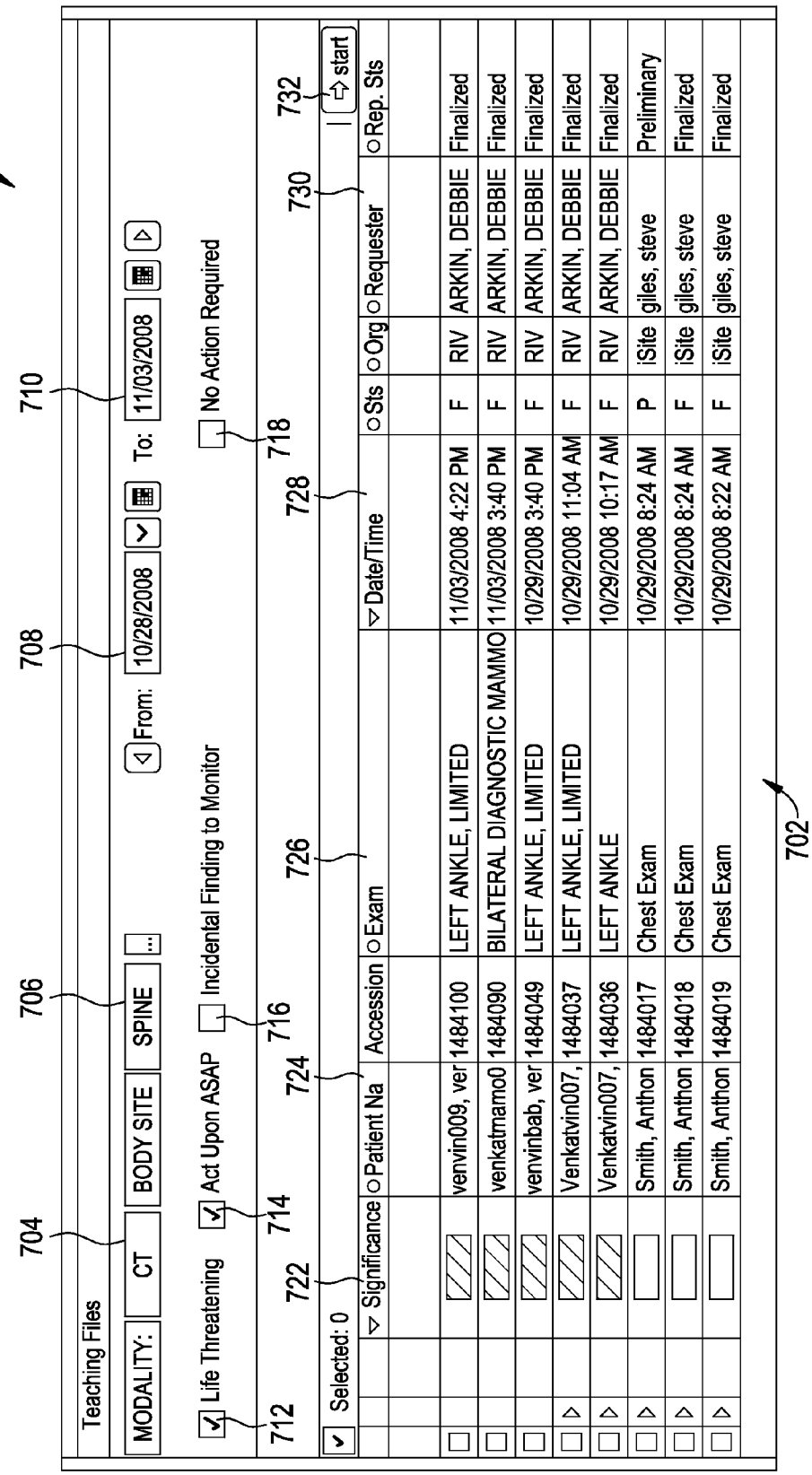
FIG. 7 is yet another screenshot of an example user interface used to convey the medical information stored and communicated in the example medical information system of FIG. 1.

FIG. 7 depicts an example user interface 700 that includes a display area 702 for entering information and for displaying identified exams. Specifically, the display area 702 includes a modality entry field 704, a body site entry field 706, a start time entry field 708, an end time entry field 710, a plurality of significance level icons 712, 714, 716 and 718 and an identified exam display area 720. The identified exam display area 720 includes a plurality of data fields or categories in which corresponding information from a corresponding exam may be positioned adjacent to. Some of the data fields and/or categories may correspond to a significance icon 722, a patient name icon 724, an exam icon 726, a date/time icon 728 and a requester icon 730. In other examples, the user interface 700 may include additional or alternative entry fields (not shown) such as, for example, patient name, medical record, etc.

In practice, initially, a healthcare practitioner enters a modality (e.g., CT) into the modality entry field 704 and a body site (e.g., chest, spine) into the body site entry field 706. To limit the time frame of the search, the healthcare practitioner then enters a start time into the start time entry field 708 and an end time into the end time entry field 710. The healthcare practitioner may then select one, some or all of the plurality of significance level icons 712, 714, 716 and 718. Next, the healthcare practitioner selects a start icon 732. Exams associated with the selected search criteria are then displayed in the identified exam display area 702. As such, the healthcare practitioner is able to access one or more exams to view previous clinical information, results and/or images, which may assist in clinical decision support.

Figure 8:
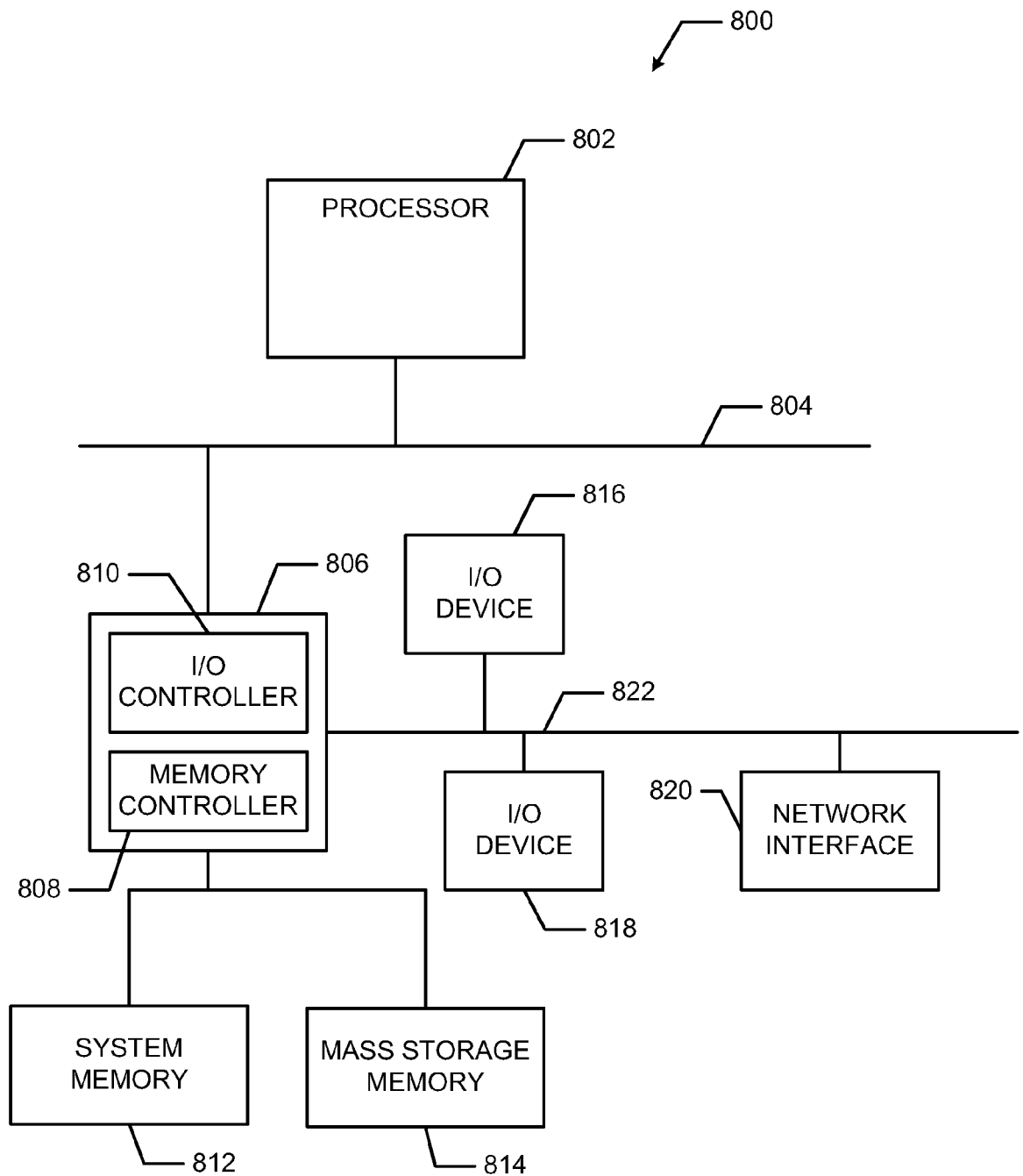
FIG. 8 is a block diagram of an example processor system that may be used to execute the machine readable instructions of FIGS. 3 and 4 to implement the example exam retriever of FIGS. 1 and/or 2.

FIG. 8 is a block diagram of the example processor system 800 that may be used to implement the apparatus and methods described herein. As shown in FIG. 8, the processor system 800 includes a processor 802 that is coupled to an interconnection bus 804. The processor 802 may be any suitable processor, processing unit or microprocessor. Although not shown in FIG. 8, the processor system 800 may be a multi-processor system and, thus, may include one or more additional processors that are identical or similar to the processor 802 and that are communicatively coupled to the interconnection bus 804.

The processor 802 of FIG. 8 is coupled to a chipset 806, which includes a memory controller 808 and an input/output (I/O) controller 810. As is well known, a chipset typically provides I/O and memory management functions as well as a plurality of general purpose and/or special purpose registers, timers, etc. that are accessible or used by one or more processors coupled to the chipset 806. The memory controller 808 performs functions that enable the processor 802 (or processors if there are multiple processors) to access a system memory 812 and a mass storage memory 814.

The system memory 812 may include any desired type of volatile and/or non-volatile memory such as, for example, static random access memory (SRAM), dynamic random access memory (DRAM), flash memory, read-only memory (ROM), etc. The mass storage memory 814 may include any desired type of mass storage device including hard disk drives, optical drives, tape storage devices, etc.

The I/O controller 810 performs functions that enable the processor 802 to communicate with peripheral input/output (I/O) devices 816 and 818 and a network interface 820 via an I/O bus 822. The I/O devices 816 and 818 may be any desired type of I/O device such as, for example, a keyboard, a video display or monitor, a mouse, etc. The network interface 820 may be, for example, an Ethernet device, an asynchronous transfer mode (ATM) device, an 802.11 device, a DSL modem, a cable modem, a cellular modem, etc. that enables the processor system 800 to communicate with another processor system.

While the memory controller 808 and the I/O controller 810 are depicted in FIG. 8 as separate blocks within the chipset 806, the functions performed by these blocks may be integrated within a single semiconductor circuit or may be implemented using two or more separate integrated circuits.

Certain example implementations contemplate methods, systems and computer program products on any machine-readable media to implement functionality described above. Certain example implementations may be implemented using an existing computer processor, or by a special purpose computer processor incorporated for this or another purpose or by a hardwired and/or firmware system, for example.

Certain example implementations include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

The example methods and apparatus described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. The example methods and apparatus described herein may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

What is claimed is:

1. A computer-implemented method, comprising:
receiving, by one or more computer processors, a medical report;
identifying and extracting key words contained within the medical report, by the one or more computer processors, the key words associated with one or more first significant findings, a modality of an image scan, and a body site;
comparing, by the one or more computer processors, the one or more first significant findings to known significant finds and, in response to the comparison, assigning a significance level to the medical report, the significance level associated with a life threatening condition, a condition to act upon as soon as possible, an incidental finding to monitor, or no action required;
comparing, by the one or more computer processors, the one or more first significant findings to records associated with prior exams to identify first prior exams of the prior exams that include information related to the one or more first significant findings, the prior exams associated with different patients than a patient associated with the medical report or the prior exams associated with the patient associated with the medical report;
associating, by the one or more computer processors, the first prior exams with the medical report;
automatically adding the medical report to a worklist, by one or more computer processors, the order in which the medical report appears in the worklist based on the significance level;
displaying, by the one or more computer processors, the worklist to a healthcare practitioner; and
visually differentiating, by the one or more computer processors, the medical report based on the significance level and a color code associated therewith, wherein the medical report and the first prior exams being selectable to assist the healthcare practitioner in clinical decision support.

2. The method as defined in claim 1, further comprising sorting the medical report and other medical reports within the worklist based on a corresponding significance level.

3. The method as defined in claim 1, wherein displaying the worklist comprises displaying a longitudinal record of the medical report and other medical reports.

4. The method as defined in claim 1, wherein the medical report is generated from voice inputs on which a speech-to-text conversion is performed.

5. The method as defined in claim 1, further comprising enabling a healthcare practitioner to edit the significance level.

6. A medical information system, comprising:
a data store in communication with one or more data entry systems to receive and store records associated with a medical report and prior exams, the data store being a non-transitory computer readable storage media;
a computer processor in communication with the data store, the computer processor configured to:
identify and extract key words contained within the medical report, the key words associated with one or more first significant findings, a modality of an image scan, and a body site;
compare the one or more first significant findings to known significant findings;
in response to the comparison, assign a significance level to the medical report, the significance level associated with a life threatening condition, a condition to act upon as soon as possible, an incidental finding to monitor, or no action required;
compare the one or more first significant findings to the records associated with the prior exams to identify first prior exams of the prior exams that include information related to the one or more first significant findings, the prior exams associated with different patients than a patient associated with the medical report or the prior exams associated with the patient associated with the medical report;
associate the first prior exams with medical report;
add the medical report to a worklist, the order in which the medical report appears in the worklist being based on the significance level; and
visually differentiate the medical report based on the significance level and a color code associated therewith; and
a display module configured to display the worklist to a healthcare practitioner, the medical report and the first prior exams being selectable to assist the healthcare practitioner in clinical decision support.

7. The medical information system as defined in claim 6, further comprising a converter to perform a speech-to-text conversion on voice inputs to generate text strings from which the medical report is generated.

8. The medical information system as defined in claim 6, further comprising a sorter to sort the medical report and other medical reports within the worklist based on a corresponding significance level.

9. A non-transitory computer readable medium having instructions stored thereon that, when executed by a computer processor, cause a machine to implement a medical information system to,
receive a medical report;
identify and extract key words contained within the medical report, the key words associated with one or more first significant findings, a modality of an image scan, and a body site;
compare the one or more significant findings to known significant findings;
in response to the comparison, assign a significance level to the medical report, the significance level associated with a life threatening condition, a condition to act upon as soon as possible, an incidental finding to monitor, or no action required;
compare the one or more first significant findings to the records associated with the prior exams to identify first prior exams of the prior exams that include information related to the one or more first significant findings, the prior exams associated with different patients than a patient associated with the medical report or the prior exams associated with the patient associated with the medical report;
associate the first prior exams with the medical report;
add the medical report to a worklist, the order in which the medical report appears in the worklist being based on the significance level;
visually differentiate the medical report based on the significance level and a color code associated therewith; and
display the worklist to a healthcare practitioner, the medical report and the first prior exams being selectable to assist the healthcare practitioner in clinical decision support.

10. The non-transitory computer readable medium as defined in claim 9 having instructions stored thereon that, when executed, cause a machine to implement a medical information system that further comprises a converter to perform a speech-to-text conversion on voice inputs to generate text strings from which the medical report is generated.

11. The non-transitory computer readable medium as defined in claim 9 having instructions stored thereon that, when executed, cause a machine to implement a medical information system that further comprises a sorter to sort the medical report and other medical reports based on a corresponding significance level.

* * * * *

UNITED STATES PATENT AND TRADEMARK OFFICE
CERTIFICATE OF CORRECTION

PATENT NO. : 8,645,157 B2  
APPLICATION NO. : 12/395403  
DATED : February 4, 2014  
INVENTOR(S) : Stephan Giles et al.

Page 1 of 1

It is certified that error appears in the above-identified patent and that said Letters Patent is hereby corrected as shown below:

In the Claims:

In Column 18, line 27 (Claim 6):   Add --the-- between "with" and "medical".

In Column 18, line 55 (Claim 9):   Add --first-- between "more" and "significant".

In Column 18, line 62 (Claim 9):   Delete "the" between "to" and "records".

Signed and Sealed this  
First Day of July, 2014

Michelle K. Lee  
*Deputy Director of the United States Patent and Trademark Office*